US00PP31611P2

(12) United States Plant Patent
Olesen et al.

(10) Patent No.: US PP31,611 P2
(45) Date of Patent: Mar. 31, 2020

(54) ***CLEMATIS* PLANT NAMED 'EVIPO093'**

(50) Latin Name: *Clematis viticella*
Varietal Denomination: Evipo093

(71) Applicants: Mogens Nyegaard Olesen, Fredensborg (DK); Raymond J. Evison, St Sampsons Vale (GB)

(72) Inventors: Mogens Nyegaard Olesen, Fredensborg (DK); Raymond J. Evison, St Sampsons Vale (GB)

(73) Assignee: POULSEN ROSER A/S, Fredensborg (DE)

( * ) Notice: Subject to any disclaimer, the term of this patent is extended or adjusted under 35 U.S.C. 154(b) by 0 days.

(21) Appl. No.: 15/999,900

(22) Filed: Sep. 10, 2018

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
See application file for complete search history.

(56) References Cited

PUBLICATIONS

UPOV hit on *Clematis* plant named 'Evipo093', QZ PBR 20172273, filed Sep. 19, 2017.*
http://www.poulsenroser.com/assortment/clematis-collections/garland/akira.aspx, downloaded Jun. 20, 2019.*

* cited by examiner

*Primary Examiner* — Anne Marie Grunberg

(57) ABSTRACT

A new *Clematis* plant with a compact growth habit, profuse, white flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

2 Drawing Sheets

Botanical classification: Genus: *Clematis*. Species: *Viticella*.

Variety denomination: 'Evipo093'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2007 and the resulting seeds were planted the following winter in a controlled environment in Guernsey, Channel Islands, United Kingdom. The new variety named 'Evipo093' originated as a single seedling from the stated cross.

The new *Clematis* plant may be distinguished from its female seed parent and male pollen parent by the following characteristics. The female seed parent has white tepals with a faint pink stripe while the new variety has white tepals with no stripe. The male seed parent grows to a height of 175 cm in one season, while the new variety grows to 130 cm in one season.

The objective of the hybridization of this *Clematis* plant was to create a new and distinct variety for nursery culture with unique qualities such as:

1. Uniform and abundant white flowers;
2. Vigorous and compact growth, making the variety suitable for container culture; and
3. Improved disease resistance.

This combination of qualities was lacking in *Clematis* plants that were in commercial cultivation and the qualities have been substantially achieved in the new variety.

'Evipo093' was selected by Mogens N. Olesen and Raymond J. Evison in their *Clematis* development program in the Channel Islands, United Kingdom in 2008. Asexual reproduction of 'Evipo093' by means of vegetative stem cuttings and traditional layering was first performed by Mogens N. Olesen and Raymond J. Evison in the Channel Islands United Kingdom nursery during the summer of 2008. This initial and subsequent asexual propagations have demonstrated that the characteristics of 'Evipo093' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo093'.

Specifically illustrated in FIG. 1 of the drawings is an open flower, tepals detached showing reproductive flower parts, flower buds at various stages of development, and a seed head.

Figure 1:
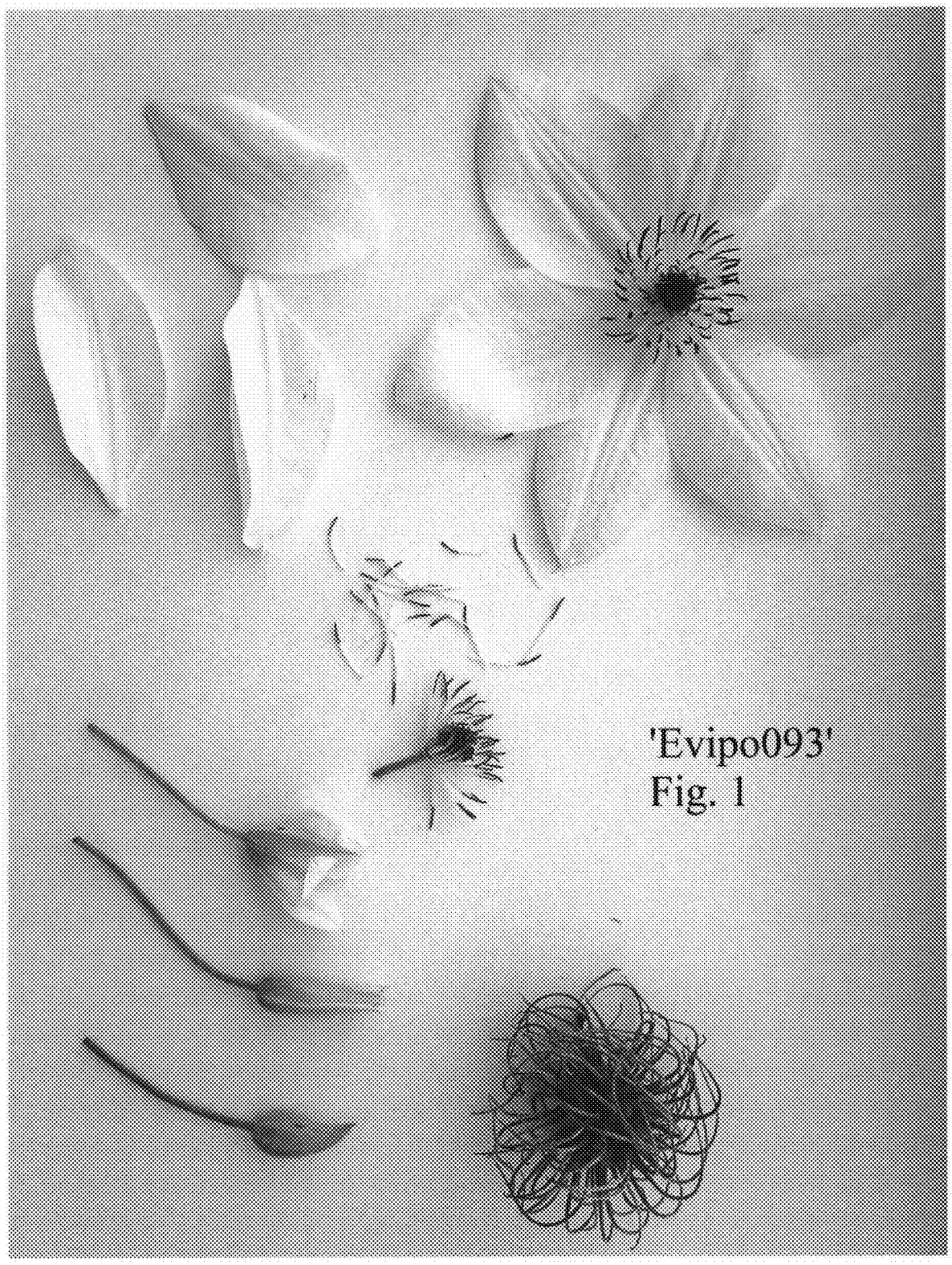
Figure 2:
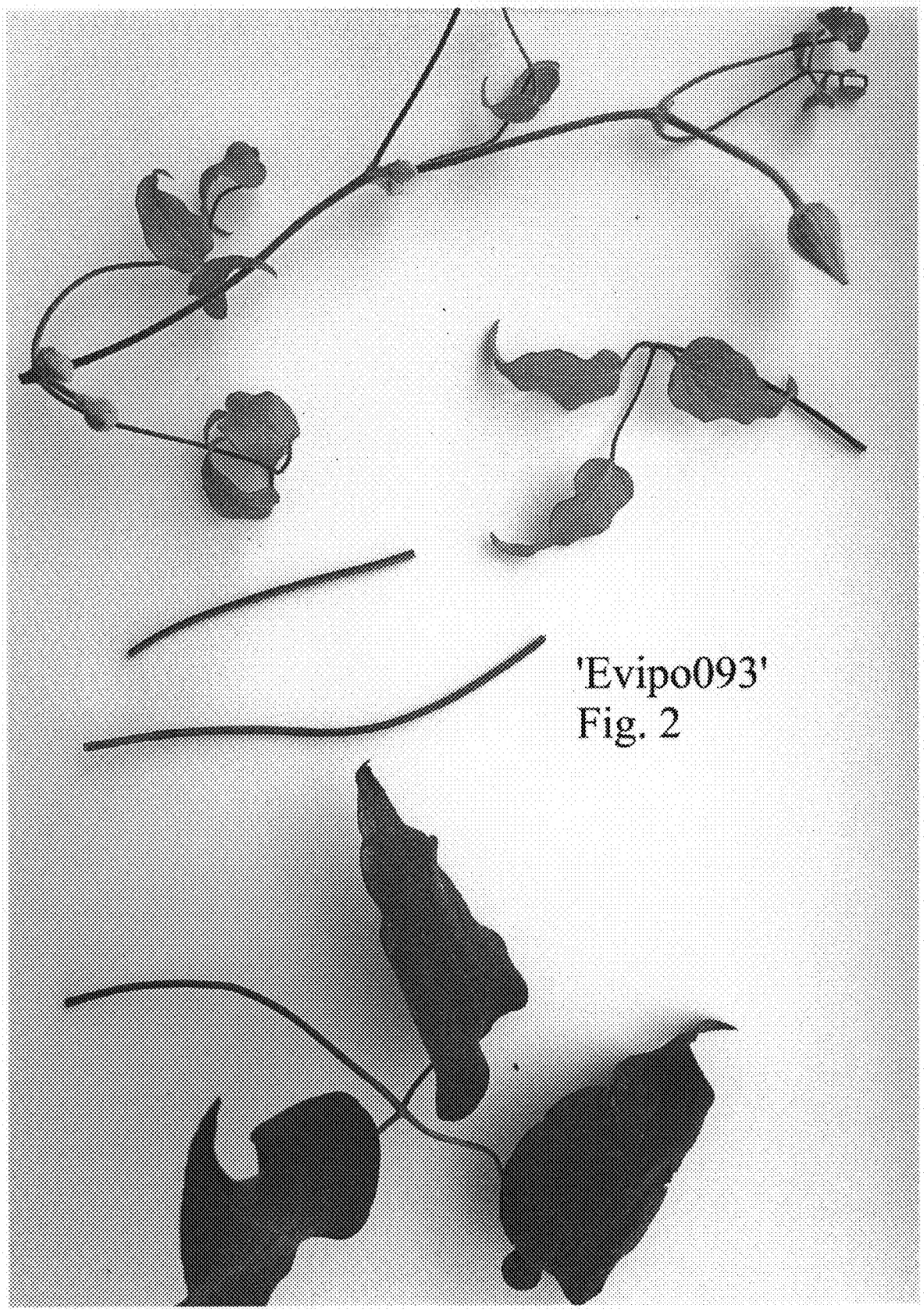
FIG. 2 shows juvenile leaves, mature leaves, and bare stems.

Illustrated plants are 2 years of age.

DETAILED DESCRIPTION OF THE VARIETY

The following is a detailed description of 'Evipo093', as observed in its growth throughout the flowering period in Denmark. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *Clematis* variety 'Evipo052' described and illustrated in U.S. Plant Pat. No. 28,600 are compared to 'Evipo093' in Chart 1.

CHART 1

| | 'Evipo093' | 'Evipo052' |
|---|---|---|
| Flower diameter | 90-130 mm | 120 mm |
| Tepal upper surface after opening | White Group 155B | White Group 155C with light intonations of Yellow-White Group 158C at the central bar |
| Tepal count | 6 | 8 |

Flower and Flower Bud

Blooming habit: Recurrent. The natural flowering period is generally from April to September.

Flower bud:
- *Size*.—Normally 22 mm in length. Bud diameter is 9 mm.
- *Bud form*.—Campanulate.
- *Bud color*.—Yellow-Green Group 145C.
- *Texture*.—Pubescent.

Pedicel:
- *Surface texture*.—Smooth, lightly pubescent.
- *Length*.—40-110 mm in length with 2 mm diameter.
- *Color*.—Yellow-Green Group 145B.
- *Strength*.—Moderately strong.

Receptacle:
- *Surface texture*.—Lightly pubescent.
- *Shape*.—Broad funnel.
- *Size*.—1 mm (h)×3 mm (w).
- *Color*.—Yellow-Green Group 145B.

Flower arrangement:
- *Location on vine*.—New growth only.
- *Borne*.—Singly, in each leaf axillary.

Flower bloom:
- *Size*.—On average, flowers are 90-130 mm in diameter and 20 mm in depth.
- *Profile*.—Flat convex.
- *Fragrance*.—None.
- *Lasting quality*.—Flowers normally remain up to 10 days on the plant.

Tepals:
- *Tepal color*.—Upon opening, the upper and under surfaces are White Group 155B. After opening, the upper and under surfaces are White Group 155B.
- *Quantity*.—Normally 6 tepals.
- *Size*.—Tepals are 50-65 mm in length by 25-35 mm wide.
- *Shape*.—Individual tepal shape is elliptic. The tepal apex is acuminate. The tepal base is typically acute.
- *Apex recurvature*.—Slightly.
- *Tepal cross section*.—Flat, or lightly reflexed.
- *Margins*.—Entire.
- *Persistence*.—Tepals drop off cleanly.

Reproductive organs:
- *Pollen*.—Quantity: Sparse. Color: Yellow-White 158A.
- *Anthers*.—Size: 4 mm in length. Color: Young flowers Violet Group 86B. At maturity Greyed-Orange Group 166A. Quantity: On average, 80.
- *Filaments*.—Color: White Group 155B. Length: 5 to 10 mm.
- *Pistils*.—Quantity: On average, 75.
- *Stigmas*.—Inferior in location relative to the length of the filaments and the height of the anthers. Color: Red-Purple Group 59A.
- *Styles*.—Color: Yellow-Green Group 145D. Length: 6 mm.

Seed head characteristics:
- *Size*.—45 mm in height. 45 mm in diameter.
- *Quantity*.—80 seeds on average.
- *Style appearance*.—Plumose, semi-erect.

Plant

Plant form: Climbing.

Plant growth: Vigorous.

Size: Seasons growth attains 130 cm in height. Average spread is 50 cm.

Stems:
- *Color*.—Juvenile stems are Greyed-Orange Group 166A. Mature stems are Greyed-Orange Group 166B.
- *Internodes*.—9-13 cm between nodes.
- *Length*.—Normally 50 cm from the base of the plant to the flowering portion of the stem.
- *Diameter*.—About 3 mm.
- *Texture*.—Mature stems are ribbed.

Plant foliage:
- *Leaf characteristics*.—Deciduous.
- *Arrangement*.—Ternate. On occasion 5 leaflets.
- *Leaf size*.—Compound leaves are about 160-270 mm (l)×200 mm (w). Leaflets are about 90 mm (l)×50 mm (w).
- *Abundance*.—On average 1 or 2 leaves per 10 cm of stem.
- *Leaf color*.—Juvenile upper Yellow-Green Group 144A. Juvenile lower Yellow-Green Group 144A. Mature upper Yellow-Green Group 147A. Mature lower Yellow-Green Group 147B.
- *Stipules*.—Absent.
- *Petioles*.—Size: Normally 90-150 mm in length by 2 mm diameter. Texture: Smooth. Color: Yellow-Green Group 146B.
- *Petioloule*.—Size: About 15-80 mm in length by 2 mm diameter. Texture: Smooth. Color: Yellow-Green Group 146B.
- *Leaflet shape*.—Elliptic. The base is rounded and cordate, the apex is acute.
- *Margin*.—Entire.
- *Surface*.—The upper side is smooth, the lower side is smooth.
- *Thickness*.—Moderate.
- *Glossiness*.—Moderately glossy.

Disease resistance: Subject to any disease that normally attacks the species. However the variety is more tolerant to *Clematis* wilt, *Ascochyta clematidina*, than some *Clematis* known to the inventors.

Cold hardiness: The variety is tolerant to USDA Hardiness Zone 6.

Heat tolerance: The variety has been found to be suitable for climate conditions found in The American Horticulture Society heat zone 7.

We claim:

1. A new and distinct variety of *Clematis* plant named 'Evipo093', substantially as described and illustrated, due to its abundant white flowers with good keepability, attractive long lasting foliage and compact growth, suitability for production from softwood cuttings in pots, durable flowers and foliage which make the variety suitable for distribution in the floral industry.

* * * * *

'Evipo093'

'Evipo093'